(12) United States Patent
Carter

(10) Patent No.: US 8,696,227 B1
(45) Date of Patent: Apr. 15, 2014

(54) SINGLE USE TOPICAL ANESTHETIC APPLICATOR

(76) Inventor: Thaddeus Carter, Ft. Collins, CO (US)

( * ) Notice: Subject to any disclaimer, the term of this patent is extended or adjusted under 35 U.S.C. 154(b) by 307 days.

(21) Appl. No.: 13/068,115

(22) Filed: May 3, 2011

(51) Int. Cl.
B43K 5/14 (2006.01)

(52) U.S. Cl.
CPC ................... *A61M 35/006* (2013.01)
USPC .................. 401/133; 604/3; 401/132; 401/41

(58) Field of Classification Search
USPC ......... 433/80, 89, 90; 424/435; 401/132–135, 401/40–41; 604/1–3
See application file for complete search history.

(56) References Cited

U.S. PATENT DOCUMENTS

| | | |
|---|---|---|
| 3,179,108 A | 4/1965 | Bloch et al. |
| 3,508,547 A | 4/1970 | Deuschle |
| 3,757,782 A | 9/1973 | Aiken |
| 3,876,314 A | 4/1975 | Nehring |
| 4,173,978 A | 11/1979 | Brown |
| 4,740,194 A | 4/1988 | Barabino et al. |
| 4,887,994 A | 12/1989 | Bedford |
| 5,112,297 A | 5/1992 | Stalcup et al. |
| 5,330,917 A * | 7/1994 | Stone .............................. 436/73 |
| 5,364,792 A * | 11/1994 | Stone .............................. 436/73 |
| 5,550,061 A * | 8/1996 | Stone .............................. 436/73 |
| 5,704,906 A * | 1/1998 | Fox .................................. 604/1 |
| 5,762,494 A | 6/1998 | Archambault |
| 5,919,152 A | 7/1999 | Zygmont |
| 6,364,862 B1 | 4/2002 | Bonilla |
| 6,409,680 B1 * | 6/2002 | Caillouette ................... 600/584 |
| 6,623,440 B1 | 9/2003 | Weldon |
| 7,008,392 B2 | 3/2006 | Beaudry |
| 7,025,521 B2 * | 4/2006 | Tsaur ............................ 401/132 |
| 7,241,065 B2 | 7/2007 | Tuffs et al. |
| 7,582,067 B2 * | 9/2009 | Van Acker ....................... 604/1 |
| 2003/0108846 A1 | 6/2003 | Hoertsch |
| 2005/0261639 A1 | 11/2005 | Herwick |
| 2006/0211978 A1 | 9/2006 | Do |
| 2009/0005454 A1 * | 1/2009 | Barshis ......................... 514/636 |

* cited by examiner

Primary Examiner — David Walczak
Assistant Examiner — Jennifer C Chiang
(74) Attorney, Agent, or Firm — Kenneth F. Pearce

(57) ABSTRACT

An applicator that dispenses a predetermined dose of topical anesthetic to a zone of tissue. When tissue is contacted, the topical anesthetic applicator also releases a visible spectrum temporary marking agent that generates a target for the pre-operative injection of a numbing dose of local anesthetic.

21 Claims, 3 Drawing Sheets

SINGLE USE TOPICAL ANESTHETIC APPLICATOR

BACKGROUND OF THE INVENTION

1. Field of the Invention

Among other things, the present invention is a topical anesthetic applicator. Preferred embodiments of the current invention dispense a topical anesthetic and release a temporary visible spectrum marking agent. When applied to tissue, the temporary visible spectrum marking agent produces a target for the preoperative injection of a numbing dose of local anesthetic into the surgical field.

2. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) U.S. Pat. No. 7,241,065—Tuffs, et al. enables an applicator for coloring antiseptic. In part, Column 3 reads, "Referring to the drawings in general and initially to FIG. 1 and FIG. 2 in particular, where like reference numerals identify like elements in the various views, a liquid applicator manifesting aspects of the invention is illustrated and designated generally by the numeral 10. The liquid applicator 10 generally includes a body 12, at least one closed ampoule for containing liquid 14 received in the body 12, and porous pad 16 secured to body 12. In the illustrated embodiment, the liquid applicator 10 also includes a porous plug 15 that contains colorant."

Tuffs teaches body 12 and porous plug 15. At the same time, among other things, the '065 patent does not teach or suggest a bulbous member, a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '065 patent does not teach or suggest an applicator with an integral handle and dosing end, wherein the dosing end has a first segment carrying topical anesthetic circumscribing a second segment carrying temporary visible marker.

2) US Published Patent Application 20050261639—Herwick discloses a medicated ink marker. Paragraph 67 reads, "The medicated ink marker 60 can fit within a holder 74 for holding the porous applicator, an example embodiment of which is shown in FIG. 8. The holder 74 has a coupling 76 for receiving the porous applicator, the specific mechanism of which can vary as understood by one of ordinary skill in the art, and can include adhesive, mechanical fastener, and the like. The holder 74 is a structure that is more easily manipulated by the user when applying the medicated ink marker 60 against the surface 12. The holder 74 represents any number of different variations of tools or implements for holding the medicated ink marker 60 while the drug or agent is applied to the surface 12. Such tools or implements can include other variations of handles or grips, as well as other elongate structures such as tongs, clamps, shafts, surgical tools, and the like, or other structures that serve the function of providing something for the user to grasp other than directly grasping the medicated ink marker 60 directly."

The Herwick Application discloses that drugs can be carried by ink marker 60. However, among other things, the '639 Application does not teach or suggest a bulbous member, a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue.

3) U.S. Pat. No. 5,112,297—Stalcup, et al. enables a topical anesthetic applicator, dispenser system, and method. In part, Column 2 reads, "Referring now to FIG. 1, a preferred embodiment of the applicator 20 for topical anesthetics is illustrated. The preferred embodiment is discussed in the context of dental applications, although it is to be understood that the invention has utility generally to apply topical anesthetics to mucosal tissue. Thus, other medical applications exist to apply anesthetic to such exemplary areas as the mucosal tissue in the nose.

The applicator 20 comprises an elongated handle 22 covered at one end thereof by an applicator member 24 characterized by an extended surface area. Preferably, the member 24 comprises a material such as a soft sponge-like material such as an open celled foam rubber or like material. One shape of the applicator member 24 suitable for this purpose is a cylindrical shape as shown in FIG. 1. Other shapes and configurations can also be employed. The cylindrical configuration is well suited to dental applications. This configuration facilitates the application of positive pressure of the applicator member 24 against the mucosal tissue, which is particularly useful to anesthetize a local area in preparation for a block injection. Obviously, the material chosen for member 24 must be non-toxic, and is preferably absorbent of the particular topical anesthetic to be applied."

Stalcup teaches shaft 22 and a chemical containing bulbous-like member 24 supported by a shaft. However, Stalcup does not teach or suggest a bulbous member having a first segment carrying a topical anesthetic circumscribing a second segment carrying temporary marker, wherein upon contact with tissue, the topical anesthetic and temporary marker are released onto a zone of the tissue. Further, the '297 patent does not teach or suggest an applicator with an integral handle and dosing end, wherein the dosing end has a first segment carrying topical anesthetic circumscribing a second segment carrying temporary visible marker.

4) U.S. Pat. No. 6,364,862—Bonilla enables a single pad for providing both an anesthetic and an antiseptic for an injection site. In part, Column 3 reads, "The single pad 10 comprises a first layer of material 12, a second layer of material 14 overlying the first layer of material 12, a third layer of material 16 overlying the second layer of material 14, an antiseptic solution 18 impregnating the first layer of material 12 for cleaning the injection site, and an anesthetic solution 20 impregnating the third layer of material 16 for anesthetizing the injection site and being used by merely turning the pad 10 over after the antiseptic solution 18 has been applied."

Bonilla teaches a pad capable of applying at least two chemical compositions. However, the '862 patent does not teach a shaft, a bulbous member, a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '862 patent does not teach or suggest an applicator with an integral handle and dosing end, wherein the dosing end has a first segment carrying topical anesthetic circumscribing a second segment carrying temporary visible marker.

5) U.S. Pat. No. 7,008,392—Beaudry enables a hemostatic cleansing swab. In part, Columns 2 and 3 read, "Hemostatic cleansing swab 10 comprises a hollow stick 12 and a wound treating element 20. Stick 12 is generally elongated and has a proximal portion 14, a proximal end 15, a distal portion 16 and a distal end 17. Proximal portion 14 of stick 12 serves as a handle during use of the swab.

Wound treating element 20 is secured to stick 12 at its distal portion 16. Wound treating element 20 comprises a wound cleaning element 22 and a hemostat-containing element 24. In the embodiment under discussion, and as seen in FIGS. 3 and 4 of the drawings, wound cleansing element 22 is in the shape of a tear-drop and is attached over distal end 17 of stick 12 and continued downwardly over the upper part of distal portion 16. Wound cleansing element 22 may be secured to the outer surface of stick 12 by frictional engagement; alternatively, an adhesive (not shown in the drawings) may be used for this purpose.

Also as illustrated in FIGS. 3 and 4, hemostat-containing element 24 is secured to the outer surface of one side of wound cleansing element 22. Preferably, a liquid impermeable material in the form of a thin layer of liquid impermeable film 32 is placed between the adjoining surfaces of the wound cleansing element and the hemostat-containing element. The presence of liquid impermeable film 32 prevents liquid released to wound cleansing element 22 during use from undesirably flowing into hemostat-containing element 24. Film 32 need not be used if it is not necessary to restrict flow of liquid from the wound cleansing element into the hemostat-containing element. It will be apparent to those skilled in the art that an adhesive can be used to secure element 24 to film 32 and to secure film 32 to element 22. Alternatively, film 32 can be heat-sealed to element 24 and the resulting heat sealed laminate can then be secured to element 22. It will be understood that, if so desired, the hemostat-containing element can be attached to the proximal portion 14 of stick 12."

Beaudry discloses shaft 12 and bulbous tip 22. Among other things, Beaudry does not teach a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '392 patent does not teach or suggest an applicator with an integral handle and dosing end, wherein the dosing end has a first segment carrying topical anesthetic circumscribing a second segment carrying temporary visible marker.

6) US Published Patent Application 20060211978—Do discloses a method for treatment of skin diseases and the like. Paragraph 18 reads, "As shown in FIG. 2, the pharmacological active agent can also be applied as a layer 16 on the swab 14 at the end of the applicator 10. The layer 16 can be on the surface only, diffused somewhat into the swab material, or completely diffused throughout the swab. The pharmacological agent can be mixed homogonously throughout the swab or can be fixed within or on the swab material on the applicator, so long as they can be dispersed after hydration onto the skin."

Do teaches shaft 12, bulbous swab 14 and pharmaceutically active layer 16 applied to the outward edge of the bulbous swab 14. However, Do does not disclose a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '978 Application does not teach or suggest an applicator with an integral handle and dosing end, wherein the dosing end has a first segment carrying topical anesthetic circumscribing a second segment carrying temporary visible marker.

7) U.S. Pat. No. 3,179,108—Bloch enables an applicator. In part, Column 3 reads, "The swab comprises a thin walled hollow thermoplastic stick 16 and a wad 17 of absorbent fibrous material secured to each end of the stick."

Among other things, Bloch does to teach a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '108 patent does not teach or suggest an applicator with an integral handle and dosing end, wherein the dosing end has a first segment carrying topical anesthetic circumscribing a second segment carrying temporary visible marker.

8) U.S. Pat. No. 3,508,547—Deuschle enables an applicator swab. In part, Column 2 reads, "The applicator 10 of this invention includes a handle portion 12, preferably a thin elongate member of substantially rigid plastic, or the like. One end of the handle is provided with an opening 14 which preferably is of an irregular shape, such as the generally trapezoidal shape illustrated . . . . A swab portion 16, preferably of an expanded foam polyurethane or similar sponge-like material, is attached to the end of the handle 12 in the are of opening 14."

Among other things, Deuschle does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '547 patent does not teach or suggest an applicator with an integral handle and dosing end, wherein the dosing end has a first segment carrying topical anesthetic circumscribing a second segment carrying temporary visible marker.

9) U.S. Pat. No. 3,757,782—Aiken enables a fluid perssurizable swab applicator for medicament, antiseptic or the like. In part, Column 2 reads, A first version of the applicator, generally designated by the reference number 10, is shown in FIGS. 1 and 1 and comprising an axially elongated tubular applicator handle rod 12 of relatively small diameter . . . the material must be chemically inert to the treatment liquid, represented by a charge 14 of antiseptic or medicament contained in tube member 12. The charge substantially fills the interior of said member between extreme opposite ends . . . ."

Among other things, Aiken does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '782 patent does not teach or suggest an applicator with an integral handle and dosing end, wherein the dosing end has a first segment carrying topical anesthetic circumscribing a second segment carrying temporary visible marker.

10) U.S. Pat. No. 3,876,314—Nehring enables a pre-filled applicator or scrubber. In part, Column 3 reads, "Referring first to FIG. 1 the applicator generally indicated at 10 is shown as comprising a tubular handle 12 preferably made of a semi-rigid plastic material, such as a medium density polyethylene, extruded or molded. The thickness of the wall of the handle 12 should be such as to afford sufficient rigidity for use as a handle to apply a required amount of pressure to a surface being treated while at the same time to permit squeezing of the handle to force liquid contained therein into the applicator head from time to time as required. With the polyethylene material just referred to, a wall thickness of about 30 mils (0.030 inch) will be adequate for accomplishment of both of these purposes, when the applicator is to be used, for example, as a surgical skin scrubber where vigorous action and relatively high rubbing pressures are involved. Other plastic materials such as polyamides (nylon) or polyvinyl chlorides also may be used. Wall thickness in all cases may be chosen for various intended uses and thinner walls are chosen when scrubbing or high pressures are not required."

Among other things, Nehring does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '314 patent does not teach or suggest an applicator with an integral handle and dosing end, wherein the dosing end has a first segment carrying topical anesthetic circumscribing a second segment carrying temporary visible marker.

11) U.S. Pat. No. 4,173,978—Brown enables a self contained antiseptic applicator swab. In part, Column 2 reads, "A foam tip 46, as seen in FIGS. 6 and 7, is preferably of a two pound density polyester foam and is provided with an adhesive strip 48 that is adhesive both on the front and back, and is porous so that the antiseptic liquid 32 can penetrate therethrough when the glass ampoule 30 is crushed and the antiseptic liquid flows through the channel 42 in the blister package and into the foam tip 46. The adhesive is of the type known as Micropore adhesive, a registered trademark of the 3M Company, and will not lose its adhesiveness when exposed to the alcohol present in the antiseptic."

Among other things, Brown does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '978 patent does not teach or suggest an applicator with an integral handle and dosing end, wherein the dosing end has a first segment carrying topical anesthetic circumscribing a second segment carrying temporary visible marker.

12) U.S. Pat. No. 4,740,194—Barabino, et al. enables a self-contained liquid swab applicator and method for its manufacture. In part, Column 3 reads, "Referring now to the drawings there is shown in FIG. 1 a self-containing liquid swab applicator 10 constructed of a hollow flexible plastic material and forming a supply liquid-containing shaft or tubing 12 and shown prepared for use. Sealed ends 14, 16 are sealed and upon removal of an adhesive tape or tab 18, the liquid 22 gravitates through an exit orifice 20 to saturate an outer surface of an adsorbent material 24 forming a swab 66, an open cell foam material or cotton form having a good quality of wickability or one that is found to permit wicking of the supply liquid that thoroughly saturates the outer surface thereof."

Among other things, Barabino does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '194 patent does not teach or suggest an applicator with an integral handle and dosing end, wherein the dosing end has a first segment carrying topical anesthetic circumscribing a second segment carrying temporary visible marker.

13) U.S. Pat. No. 4,887,994—Bedford enables applicator swabs and method of making same. In part, Columns 2 and 3 read, "When impregnated with an antibacterial or disinfectant fluid, the applicator swabs of the present invention are advantageously packaged in a fluid-impervious package or pouch 31. The pouch is sealed at its periphery to completely encase the plurality of applicator swabs 35, 37 and 39 contained therein. The pouch provides a disinfected environment for storage of the swabs 35, 37 and 39. The pouch may be opened by tearing along a tear line 33, for example, or by utilizing any other convenient opening device. The package 31 is preferably made of an aluminum foil material that is well known for this use.

Each of the applicators 35, 37 and 39 stored within the pouch 31 may contain an antigermicide or disinfectant solution 41, or any other solution that can be conveniently applied by a swab applicator of the type illustrated herein. Besides the solution contained within the open-cell foam applicators 35, 37 and 39, a certain amount of the solution might be found in the bottom of the pouch. This type of disinfected packaging of the applicator swabs is designed to encourage the swabs to be thrown away."

Among other things, Bedford does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '994 patent does not teach or suggest an applicator with an integral handle and dosing end, wherein the dosing end has a first segment carrying topical anesthetic circumscribing a second segment carrying temporary visible marker.

14) U.S. Pat. No. 5,762,494—Archambault enables an applicator device and method. In part, Column 4 reads, "The anesthetic delivery member 10 is a member formed of material which can retain and deliver an amount of anesthetic suitable for use in the mouth, such as lidocaine. Preferably the delivery member 10 is pre-dosed with a measured amount of anesthetic and packaged in suitable material to create a relatively long shelf life, the package being opened at the time of use, but the device could also be used where the anesthetic is applied to the delivery member 10 from a common container or source. The delivery member 10 may be composed of any suitable material capable of retaining and delivering the anesthetic and of being fixedly attached to a second retention means 30, such as spun or woven cotton or other natural or synthetic fibers, polymer or natural foam or sponge material, or polymer-based gels or matrices. The delivery member 10 may be shaped in various configurations such as round, oval, square or rectangular, and can be spheroid or relatively flat. Preferably the delivery member 10 is generally round or ovoid to better match the curve of the alveolar mucosa area. Such delivery members 10 are well known in the art."

Among other things, Archambault does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '494 patent does not teach or suggest an applicator with an integral handle and dosing end, wherein the dosing end has a first segment carrying topical anesthetic circumscribing a second segment carrying temporary visible marker.

15) U.S. Pat. No. 5,919,152—Zygmont enables antibacterial swabs. In part, Column 2 reads, "Swabs, especially cotton swabs can be rendered less susceptible to microbial contamination by impregnating antibacterial agents onto cotton or other absorbent coverings surrounding ends of the swab.

FIG. 1 illustrates a typical swab with an elongate stem 2 having first and second ends 4, 6 at opposite extremities from one another. An absorbent covering 8 surrounds each of the first and second ends. Cotton is the most preferred absorbent covering. However, synthetic or other natural materials with flexible and absorbent properties can also be used. For example, the absorbent covering could be formed of rayon fibers, polyester, polyurethane or other foamed or fibered synthetic polymers."

Among other things, Zygmont does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '152 patent does not teach or suggest an applicator with an integral handle and dosing end, wherein the dosing end has a first segment carrying topical anesthetic circumscribing a second segment carrying temporary visible marker.

16) U.S. Pat. No. 6,623,440—Weldon enables a topical applicator and method of use. In part, Column 2 reads, "To perform the method, the physician first dips the absorbent means of the applicator into topical anesthetic. The physician then lightly abrades the desired oral site with the abrasive means, followed immediately by applying the absorbent means containing the topical anesthetic to the abraded mucosal area. The application of the topical anesthetic is followed by an injection given by an injection device in which the depth of the injection is automatically limited to penetrate only into the area anesthetized by the topical. As a result, the patient experiences greatly reduced discomfort and pain."

Based on the current record, among other things, Weldon does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '440 patent does not teach or suggest an applicator with an integral handle and dosing end, wherein the dosing end has a first segment carrying topical anesthetic circumscribing a second segment carrying temporary visible marker.

17) US Published Patent Application 20030108846—Hoertsch discloses a disposable oral hygiene device and methods of making same. Paragraph 28 reads, "As representatively illustrated in FIGS. 1-4, the disposable, hand-held, oral hygiene device 20 of the present invention can include among its elements a swab 50 suitable for cleaning teeth, gums, and the mouth in general. The swab 50 can be constructed of any material suitable for such use, including such materials as, for example, cotton, rayon, wood pulp, polymeric substances such as nonwoven fabrics, foam sponges, thermoplastics, or the like. The swab 50 defines an outer surface 51 which can be smooth or rough, and may contain tufts, ridges, projections or other topographical characteristics giving the outer surface 51 a three-dimensional character, thereby imparting the desired cleaning properties to the device 20. In particular embodiments, the outer surface 51 can be textured to facilitate removal of residue and film from the teeth, gums, tongue, and other areas of the mouth."

Among other things, Hoertsch does not teach a first segment of the dosing end of the bulbous member and a second segment of the bulbous member carrying temporary marker circumscribed by the first segment, wherein upon contact with tissue, the topical anesthetic and temporary marker are released onto a zone of the tissue. Further, the '846 Application does not teach or suggest an applicator with an integral handle and dosing end, wherein the dosing end has a first segment carrying topical anesthetic circumscribing a second segment carrying temporary visible marker.

SUMMARY OF THE INVENTION

The present invention provides a single use topical anesthetic applicator capable of carrying and dispensing a predetermined dosage of topical anesthetic to a zone of tissue. Select embodiments of the current invention are particularly useful for oral tissue surgical fields. Along with the topical anesthetic, the topical anesthetic applicator also carries a visible spectrum temporary marking agent that is released when the topical anesthetic is dispensed onto the tissue. The temporary marking agent applied to the tissue generates a target for the preoperative injection of a numbing dose of local anesthetic into the surgical field.

An aspect of a preferred embodiment of the present invention is to provide a single use topical anesthetic applicator that also includes a temporary visible spectrum marking agent for marking a zone of tissue contacted by the single use topical anesthetic applicator.

Still another aspect of a preferred embodiment of the present invention is to provide a single use topical anesthetic applicator that dispenses a predetermined dose of topical anesthetic to a zone of tissue for lessening the pain attributed to a subsequent injection of local anesthetic into the operating field.

It is another aspect of a preferred embodiment of the present invention to provide a single use topical anesthetic applicator capable of dispensing a minimal safe and effective dosage of a topical anesthetic about the operating field such that the unpleasant taste of topical anesthetic and the numbing of tissue not associated with the surgical field are reduced.

Yet another aspect of preferred embodiments of the present invention is to provide a single use topical anesthetic applicator capable of eliminating cross contamination between different patients.

Yet still another aspect of preferred embodiments of the present invention is to provide a single use topical anesthetic applicator that improves the patient's comfort and satisfaction associated with the operation.

It is still another aspect of a preferred embodiment of the present invention to provide a single use topical anesthetic applicator capable of reducing the patient's preoperative anxiety.

An embodiment of the present invention can be described as a single use applicator for applying a topical anesthetic and a visible spectrum temporary marker to oral tissue; the single use applicator comprising: a) a shaft having a depression at an end thereof; b) a bulbous member connected to the shaft and circumscribing the depression; the bulbous member further comprising a segment distal from the bulbous member's connection to the shaft; the segment comprising a predetermined dosage of the topical anesthetic, wherein upon contact with a zone of the oral tissue, the segment dispenses the predetermined dosage for absorption by the zone; and c) a capsule contacting the depression and containing the visible spectrum temporary marker, wherein the bulbous member encircles the capsule, and wherein upon contact between the bulbous member and the oral tissue, the capsule is broken and the visible spectrum temporary marker is released about a midsection of the zone.

Another embodiment of the present invention can be described as a single use applicator for applying a topical anesthetic and a temporary marker to oral tissue; the single use applicator comprising: a) a compartmentalized bulbous member comprising an attachment end and dosing end opposite the attachment end; the compartmentalized bulbous member further comprising: i) a generally cylindrical channel extending inwardly from the attachment end and toward the dosing end; ii) a first compartment forming the attachment end and circumscribing the channel; iii) a second compartment positioned about the dosing end and carrying a predetermined dosage of the topical anesthetic, wherein upon contact with a zone of the oral tissue, the second compartment dispenses the predetermined dosage for absorption by the zone; and iv) a third compartment positioned about the dosing end and carrying the temporary marker, wherein upon contact between the compartmentalized bulbous member and the oral tissue, the temporary marker is released about the zone; and b) a shaft engaging the channel.

Yet another embodiment of the present invention can be described as an integral single use applicator for applying a topical anesthetic and a temporary marker to tissue; the integral single use applicator comprising: a) a first segment, positioned about a dosing end of the integral single use applicator, carrying a predetermined dosage of the topical anesthetic, wherein upon contact with a zone of the tissue, the first segment dispenses the predetermined dosage for absorption by the zone; b) a second segment, positioned about a dosing end of the integral single use applicator, carrying the temporary marker, wherein upon contact between the integral single use applicator and the tissue, the temporary marker is released into the zone; c) a handle segment supporting the first segment and the second segment.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the current invention is a single unit topical anesthetic applicator. Topical anesthetic applicators in accord with the present invention can have bulbous, cylindrical or other dimensioned dosing ends. Select preferred embodiments of the current invention can have an integral single unit handle and dosing end while other preferred embodiments include a handle that is distinct from the dosing end. The dosing end of the single use applicator carries a topical anesthetic, such as lidocaine, benzocaine, tetracaine, menthol or peppermint oil for anesthetizing a zone of tissue, such as a zone of oral tissue.

Within the scope of the present invention, dosing ends of preferred embodiments of the single use topical anesthetic applicators also include a segment, compartment or capsule carrying a visible spectrum temporary marker for release onto the zone of tissue for marking the zone of tissue having the topical anesthetic dispensed thereon. Among other things, the presence of the temporary marker on the tissue indicates the location of the application of the topical anesthetic to tissue. The temporary marker also generates a target for the dentist or surgeon to use when injecting local anesthetic into the operating field.

Figure 1:
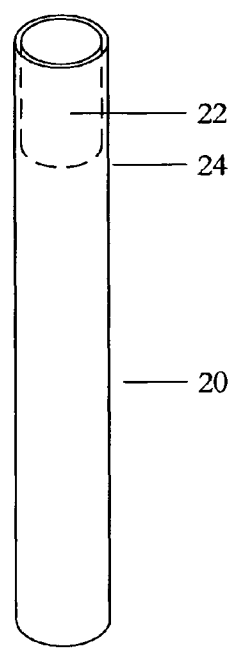
FIG. 1 is a frontal perspective of a shaft (20) that can be incorporated into a preferred embodiment of the present invention.

FIG. 1 is a frontal perspective of a shaft (20) that can be incorporated into a preferred embodiment of the present invention. Shaft (20) can include recess (22) at end (24). Shaft (20) can be manufactured of cotton, fabric, paper, wood or polymer.

Figure 2:
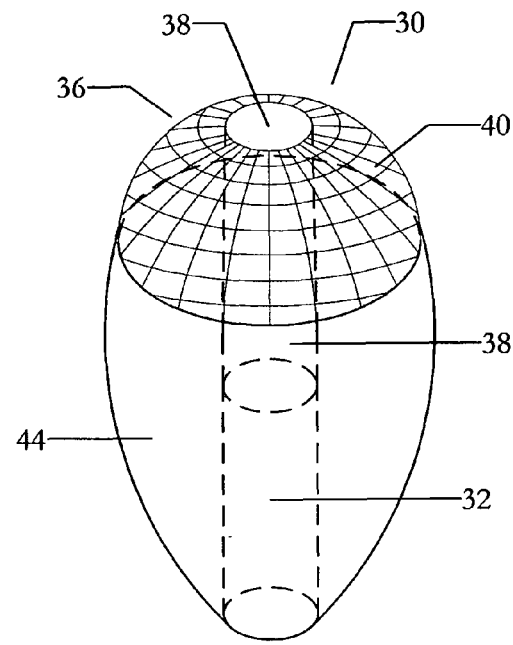
FIG. 2 is a frontal perspective of dosing member (30) for a preferred embodiment of the present invention.

FIG. 2 is a frontal perspective of dosing member (30) for a preferred embodiment of the present invention. As shown in FIG. 2, dosing member (30) is bulbous. Although not shown in FIG. 2, other embodiments of the present invention can include dosing members with geometries other than bulbous shapes.

Dosing member (30) can be provided with channel (32) capable of receiving end (24) of shaft (20). In this select preferred embodiment, end (36) of dosing member (30) is distal from end (24) of shaft (20). As shown in FIG. 2, segment or capsule (38) is positioned about a midsection of end (36). However, when engineering parameters require, segment or compartment (38) can be positioned away from the midsection of end (36). In select preferred embodiments, an end of capsule (38) can be partially seated in recess or depression (22) of shaft (20).

Marker segment or compartment (38) contains a temporary marking agent or marker. In select preferred embodiments, temporary marker is a visible spectrum marking agent selected from the group of FDA (Food and Drug Administration) approved food colorants, such as FDA red dye number 5.

In select preferred embodiments, capsule (38) is circumscribed by dosing segment (40). Dosing segment (40) carries topical anesthetic. When dosing compartment (40) of dosing member (30) contacts tissue, the topical anesthetic is dispensed to the zone of tissue contacted by dosing segment (40) of dosing member (30) and capsule (38) simultaneously releases visible spectrum marking agent on to the zone of tissue contacted by the dosing segment (40) of dosing member (30).

In select preferred embodiments, dosing member (30) also includes support segment or structure (44). Support segment (44) can be manufactured of a cotton fiber or a polymer foam or fiber, such as polyester. Support segment (44) does not contain topical anesthetic or marking agent.

Dosing segment (40) can be manufactured of cotton or polymer capable of containing and segregating the topical anesthetic from the support segment (44) and the marker segment (38) until contact between dosing segment (40) and the tissue. Select preferred embodiments of dosing compartment (40) carry a minimal safe and effective amount of predetermined dosage of topical anesthetic. Some preferred embodiments of the dosing member (30) are capable of carrying from about 1 milligram to about 5 milligrams of lidocaine capable of numbing a zone of oral tissue. Other preferred embodiments of the dosing member (30) are capable of carrying approximately 20% benzocaine or less.

Still other preferred embodiments of the dosing member (30) are capable of carrying approximately 2% lidocaine or less.

Marker segment or capsule (38) can be manufactured of cotton, paper, polymer or gelatin capable of containing and segregating the temporary visible marking agent from the support segment (44) and the dosing segment (40) until contact between dosing segment (40) and the tissue. Select embodiments of marker segment (38) are capable of carrying from about 1 milliliter to about 3 milliliters of visible spectrum temporary marking agent. When dosing segment (40) contacts a zone of tissue, marker segment (38) releases marking agent into the zone of contact.

Figure 3:
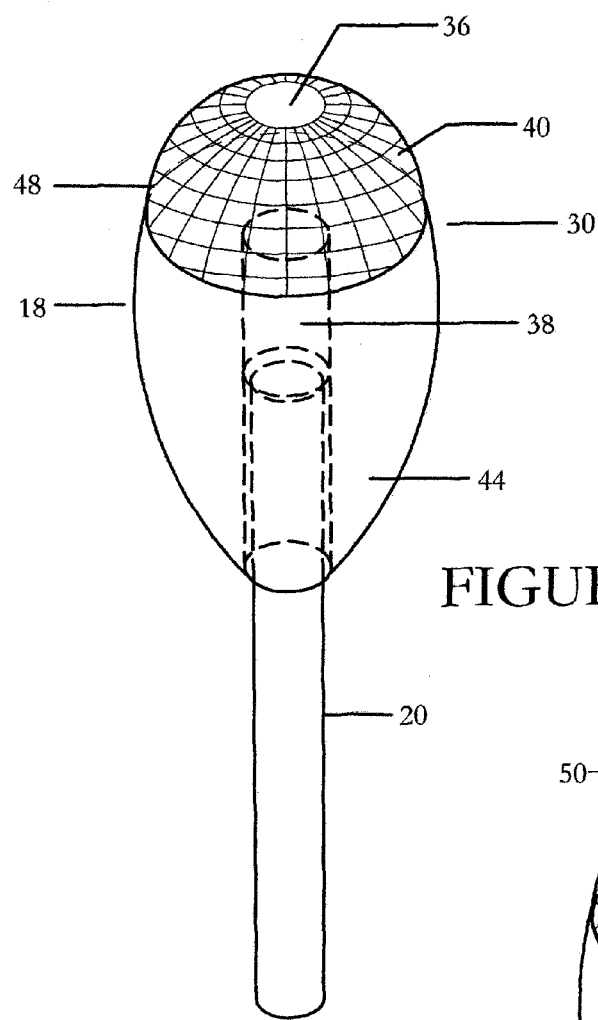
FIG. 3 portrays a frontal perspective of a preferred embodiment of single use applicator (18).

FIG. 3 portrays a frontal perspective of a preferred embodiment of single use applicator (18). Bulbous dosing member (30) is attached to shaft (20). As shown in FIG. 3, marker segment (38), dosing segment (40) and support segment (44) jointly form outward surface (48) of dosing member (30).

Figure 4:
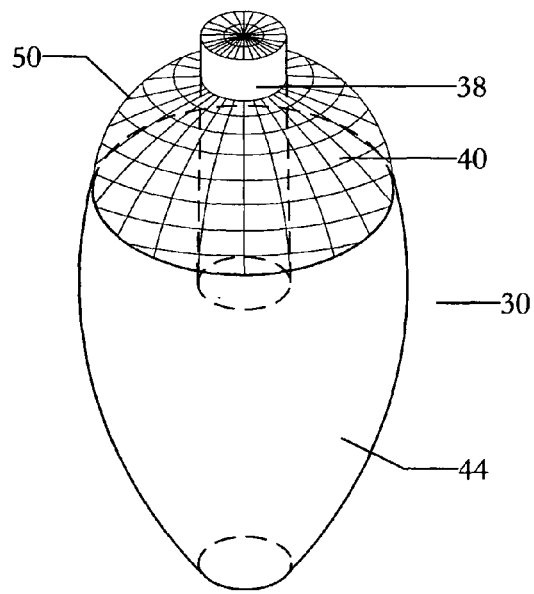
FIG. 4 is a frontal perspective of another preferred embodiment of dosing member (30).

FIG. 4 is a frontal perspective of another preferred embodiment of dosing member (30). Dosing member (30) can be attached to shaft (20) (not shown in this view). As shown in FIG. 4, marker segment (38) extends beyond an outward surface (50) of dosing segment (40).

Figure 5:
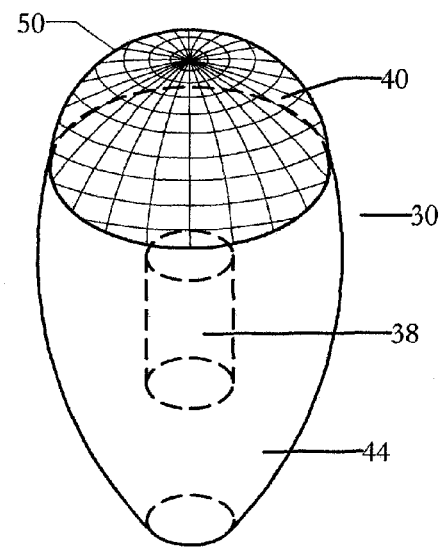
FIG. 5 is a frontal perspective of still another preferred embodiment of dosing member (30).

FIG. 5 is a frontal perspective of still another preferred embodiment of dosing member (30). Dosing member (30) can be attached to shaft (20) (not shown in this view). In the practice of the embodiment disclosed in FIG. 5, until dosing member (30) contacts a zone of tissue, marker segment (38) remains inward of outward surface (50) of dosing segment (40). When outward surface (50) of dosing segment (40) contacts a zone of tissue, marker segment (38) is forced against outward surface (50)—allowing the dispensing of both topical anesthetic and marking agent to the zone.

Figure 6:
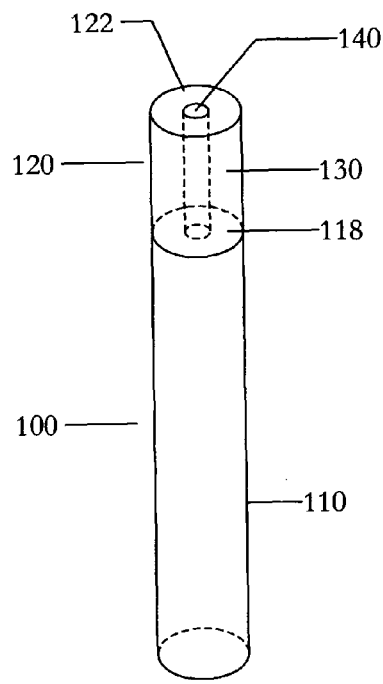
FIG. 6 is a frontal perspective of an embodiment of single use applicator (100) including handle segment (110) and dosing end (120).

FIG. 6 is a frontal perspective of a preferred embodiment of single unit-single use applicator (100) where handle segment (110) and dosing end (120) are integral components of single unit-single use applicator (100). In select preferred embodiments, barrier (118) can segregate dosing end (120) from handle segment (110). Depending on engineering parameters, barrier (118) can be physical or chemical. Dosing end (120) is provided with first segment (130) and second segment (140). In select preferred embodiments, handle segment (110) and first segment (130) can be manufactured of cotton, paper and/or polymer.

As shown in FIG. 6, second segment or capsule (140) is positioned about the midsection of outward surface (122) dosing end (120). However, when engineering parameters require, second segment (140) can be positioned away from the midsection of dosing end (120). As disclosed in FIG. 6, first segment (130) and second segment (140) jointly form the outward surface (122) of dosing end (120).

Second segment or compartment (140) contains a temporary marking agent or marker. In select preferred embodiments, temporary marker is a visible spectrum marking agent selected from the group of FDA approved food colorants, such as FDA red dye number 5.

First segment (130) carries topical anesthetic. In select preferred embodiments, second segment (140) is circumscribed by first segment (130). In practice, when dosing end (120) contacts tissue, the topical anesthetic is dispensed to the zone of tissue contacted by first segment (130) and second segment (140) releases visible spectrum marking agent on to the zone of tissue contacted by the first segment (130) of single use applicator (100).

Select preferred embodiments of first segment (130) carry a minimal safe and effective amount of predetermined dosage of topical anesthetic. Some preferred embodiments of the first segment (130) are capable of carrying from about 1 milligram to about 5 milligrams of lidocaine capable of numbing a zone of oral tissue. Other preferred embodiments of first segment (130) are capable of carrying approximately 20% benzocaine or less. Still other preferred embodiments of first segment (30) are capable of carrying approximately 2% lidocaine or less.

Second segment (140) can be manufactured of cotton, paper, polymer or gelatin capable of containing and segregating the temporary visible marking agent from the first segment (130) until contact between first segment (130) and the tissue. Select embodiments of second segment (140) are capable of carrying from about 1 milliliter to about 3 milliliters of visible spectrum temporary marking agent.

Figure 7:
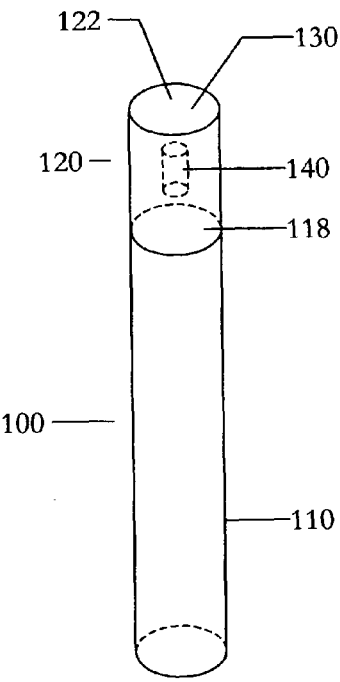
FIG. 7 is a frontal perspective of another embodiment of single use applicator (100).

FIG. 7 is a frontal perspective of a preferred embodiment of single use applicator (100). In the FIG. 7 embodiment, second segment (140) is surrounded by first segment (130). When dosing end (120) contacts tissue, the topical anesthetic is dispensed to the zone of tissue contacted by first segment (130) and second segment (140) releases visible spectrum marking agent that flows through first segment (130) and on to the zone of tissue contacted by the first segment (130) of single use applicator (100).

Figure 8:
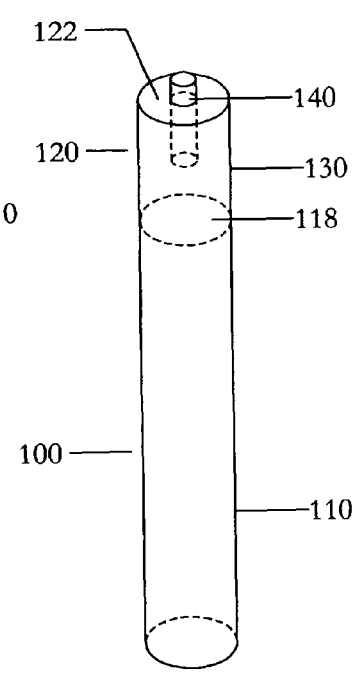
FIG. 8 is a frontal perspective of another embodiment of single use applicator (100).

FIG. 8 is a frontal perspective of a preferred embodiment of single use applicator (100). In the FIG. 8 embodiment, second segment (140) extends beyond outward surface (122) of dosing end (120). When dosing end (120) contacts tissue, the topical anesthetic is dispensed to the zone of tissue contacted by first segment (130) and second segment (140) releases visible spectrum marking agent on to the zone of tissue contacted by the first segment (130) of single use applicator (100).

Having disclosed the invention as required by Title 35 of the United States Code, Applicant now prays respectfully that Letters Patent be granted for his invention in accordance with the scope of the claims appended hereto.

What is claimed is:

1. A single use applicator for applying a topical anesthetic and a visible spectrum temporary marker to oral tissue; said single use applicator comprising:
    a) a shaft having a depression at an end thereof;
    b) a bulbous member connected to said shaft and circumscribing said depression; said bulbous member further comprising a segment distal from said bulbous member's connection to said shaft; said segment comprising a predetermined dosage of said topical anesthetic, wherein upon contact with a zone of said oral tissue, said segment dispenses said predetermined dosage for absorption by said zone; and
    c) a capsule contacting said depression and containing said visible spectrum temporary marker, wherein said bulbous member encircles said capsule, and wherein upon contact between said bulbous member and said oral tissue, said capsule is broken and said visible spectrum temporary marker is released about a midsection of said zone.

2. The invention of claim 1, wherein said segment contains a minimal safe and effective amount of said predetermined dosage of said topical anesthetic.

3. The invention of claim 2, wherein said capsule contains from about 1 milliliter to about 3 milliliters of said visible spectrum temporary marker.

4. The invention of claim 3, wherein said predetermined dosage is:
    a) from about 1 milligram to about 5 milligrams of lidocaine; or
    b) approximately 20% benzocaine or less; or
    c) approximately 2% lidocaine or less.

5. The invention of claim 3, wherein said segment and said capsule jointly form part of a portion of an outward surface of said bulbous member.

6. The invention of claim 3, wherein until said bulbous member contacts said oral tissue, said capsule is inward of said outward surface of said bulbous member.

7. The invention of claim 3, wherein said capsule extends beyond an outward surface of said segment.

8. A single use applicator for applying a topical anesthetic and a temporary marker to oral tissue; said single use applicator comprising:
   a) a compartmentalized bulbous member comprising an attachment end and dosing end opposite said attachment end; said compartmentalized bulbous member further comprising:
      i) a generally cylindrical channel extending inwardly from said attachment end and toward said dosing end;
      ii) a first compartment forming said attachment end and circumscribing said channel;
      iii) a second compartment positioned about said dosing end and carrying a predetermined dosage of said topical anesthetic, wherein upon contact with a zone of said oral tissue, said second compartment dispenses said predetermined dosage for absorption by said zone; and
      iv) a third compartment positioned about said dosing end and carrying said temporary marker, wherein upon contact between said compartmentalized bulbous member and said oral tissue, said temporary marker is released about said zone; and
   b) a shaft engaging said channel.

9. The invention of claim 8, wherein said second compartment contains at least a minimal safe and effective amount of said predetermined dosage of said topical anesthetic.

10. The invention of claim 9, wherein said second compartment encircles said third compartment.

11. The invention of claim 10, wherein said third compartment contains from about 1 milliliter to about 3 milliliters of said temporary marker.

12. The invention of claim 10, wherein said second compartment and said third compartment jointly form a portion of an outward surface of said compartmentalized bulbous member.

13. The invention of claim 10, wherein until said compartmentalized bulbous member contacts said oral tissue, said third compartment is inward of said second compartment.

14. The invention of claim 10, wherein said third compartment extends beyond an outward surface of said second compartment.

15. An integral single use applicator for applying a topical anesthetic and a temporary marker to tissue; said integral single use applicator comprising:
   a) a first segment, positioned about a dosing end of said integral single use applicator, carrying a predetermined dosage of said topical anesthetic, wherein upon contact with a zone of said tissue, said first segment dispenses said predetermined dosage for absorption by said zone of tissue, and wherein said topical anesthetic is governmentally approved for use in humans;
   b) a second segment carrying said temporary marker, proximate said dosing end and contacting said first segment, wherein upon contact between said integral single use applicator and said tissue, said temporary marker is released into said zone of tissue, and wherein said temporary marker is governmentally approved for use in humans;
   c) a handle segment supporting said first segment and said second segment.

16. The invention of claim 15, wherein said first segment contains at least a minimal safe and effective amount of said predetermined dosage of said topical anesthetic.

17. The invention of claim 16, wherein said handle segment comprises a diameter equivalent to said diameter of said first segment.

18. The invention of claim 17 further comprising a barrier between said handle segment and said first segment.

19. The invention of claim 18, wherein said first segment and said second segment form a portion of an outward surface of said dosing end.

20. The invention of claim 18, wherein until said integral single use applicator contacts tissue, said second segment is inward of an outward surface of said first segment.

21. The invention of claim 20, wherein said second segment extends beyond an outward surface of said first segment.

* * * * *